United States Patent [19]
Clubb

[11] Patent Number: 5,990,323
[45] Date of Patent: Nov. 23, 1999

[54] PREPARATION OF AMINES

[75] Inventor: Clyde Neal Clubb, Longview, Tex.

[73] Assignee: Eastman Chemical Company, Kingsport, Tenn.

[21] Appl. No.: 09/178,110

[22] Filed: Oct. 23, 1998

[51] Int. Cl.$^6$ .................................................. C07D 307/02
[52] U.S. Cl. ............................................................. 549/491
[58] Field of Search ............................................. 549/491

[56] References Cited

U.S. PATENT DOCUMENTS 4,963,672 10/1990 Merger et al. .
5,068,398 11/1991 Merger et al. .
5,166,443 11/1992 Merger et al. .

FOREIGN PATENT DOCUMENTS 91-10848A 4/1997 Japan .

OTHER PUBLICATIONS

Freifelder, Morris, Practical Catalytic Hydrogeneration, John Wiley & Sons, Inc. 1971, pp. 333–345.

Primary Examiner—Amelia Owens
Attorney, Agent, or Firm—Michael J. Blake; Harry J. Gwinnell

[57] ABSTRACT

Disclosed is a process for the preparation of an amine by contacting in a reaction zone a water-soluble aldehyde, water, ammonia and hydrogen in the presence of a supported ruthenium catalyst at elevated temperature and pressure. The process is particularly useful for the preparation of 3-(aminomethyl)tetrahydrofuran by contacting an aqueous solution of 3-formyltetrahydrofuran with ammonia and hydrogen at elevated temperature and pressure in the presence of a supported ruthenium catalyst. The use of a supported ruthenium catalyst has been found to avoid the problem of catalyst leaching encountered when a nickel catalyst is used.

7 Claims, No Drawings

PREPARATION OF AMINES

FIELD OF THE INVENTION

This invention pertains to a novel process for preparation of amines by contacting a water-soluble aldehyde with ammonia and hydrogen in the presence of a catalyst. More specifically, this invention pertains to the synthesis of amines by contacting an aqueous solution of a water-soluble aldehyde with ammonia and hydrogen at elevated temperature and pressure in the presence of certain ruthenium catalysts.

BACKGROUND OF THE INVENTION

The preparation of amines by the reductive amination of aldehydes using nickel-based catalysts is well known as shown, for example, by Freifelder, Morris, *Practical catalytic Hydrogenation,* John Wiley & Sons, Inc. 1971, pages 333–345, and has been utilized to manufacture a variety of amines such as 2,2-dimethyl-3-aminopropanol from hydroxypivaldehyde. Japanese Patent Publication JP 91-10848 A discloses the reductive amination of FTHF with aqueous ammonia using nickel, palladium, and platinum catalysts. Although this patent document claims better selectivity for the aqueous system, the best selectivity achieved by the use of palladium or platinum catalysts was 77.4% with 5% palladium on carbon at 30° C. a higher selectivity of 99.5% was reported for Raney nickel at 60° C. All of the examples were batch autoclave experiments and no problems with product isolation or catalyst instability resulting from the use of Raney nickel were mentioned.

U.S. Pat. Nos. 4,963,672 and 5,068,398 describe the reductive amination of 5-formylvalerates in liquid ammonia using a supported ruthenium catalyst. These patents teach that the disclosed processes are carried out at relatively high total pressures of 40 to 100 bar (580 to 1450 pounds per square inch-psi). The examples contained in the patents employed total pressures of 98 to 99 bar. U.S. Pat. No. 5,068,398 discloses a comparative example that demonstrates leaching of nickel from a supported nickel catalyst. U.S. Pat. No. 5,166,443 describes a two-step process wherein certain 2,2-disubstituted-4-cyanobutanal compounds are converted to their corresponding diamines. The first step involves treating the cyanobutanal with ammonia in the presence of an acidic heterogeneous catalyst. The resulting material then is fed to a hydrogenation zone which preferably uses a ruthenium catalyst. Again, the pressures are relatively high at 50 to 500 bar (725–7250 psi), preferably 100 to 350 bar and most preferably from 150 to 300 bar. In the examples of U.S. Pat. No. 5,166,443, the hydrogenation zone is operated at a pressure of 200 or 250 bar.

Initial attempts to prepare 3-(aminomethyl) tetrahydrofuran (AMTHF) by contacting an aqueous solution of 3-formyltetrahydrofuran (FTHF) with ammonia and hydrogen in the presence of conventional Raney nickel or supported nickel catalysts did not give satisfactory results due to significant leaching of nickel into the product. In addition to losing catalyst, product isolation and purification becomes more difficult due to precipitation of nickel salts upon removal of the excess ammonia and water. During removal of the ammonia and water by distillation, pale green salts precipitate and must be removed by distillation, filtration, or both.

The FTHF from which AMTHF may be prepared preferably is used in the form of an aqueous solution. As is disclosed by W. A. Beavers in U.S. patent application Ser. No. 944,653 filed Oct. 6, 1997, FTHF may be prepared by hydroformylation of 2,5-dihydrofuran in the presence of a rhodium-phosphine catalyst and an organic, water-immiscible, hydroformylation solvent. Recovery of FTHF by distillation in the presence of the hydroformylation solvent results in the formation of hemiacetal oligomers and an overall significant yield loss. Thus, the FTHF product preferably is recovered by first extracting the hydroformylation product solution with water to produce an aqueous solution of FTHF. The use of this aqueous solution of FTHF in chemical processes wherein the FTHF is converted to other compounds such as AMTHF is a particularly efficient means for producing such other compounds.

BRIEF SUMMARY OF THE INVENTION

In developing a process for the production of AMTHF from an aqueous solution of FTHF, it was discovered that AMTHF can be produced in good yields and conversions from FTHF and ammonia in the presence of water using a catalyst comprising ruthenium on a catalyst support material and relatively mild conditions of pressure and temperature. The use of a supported ruthenium catalyst has been found to avoid the problem presented by the presence of catalyst particulate matter during product isolation and purification. It is believed that this discovery has a more general application to the conversion of water-soluble aldehydes to amines by reductive amination in the presence of water. More specifically, this discovery can be applied to aqueous aldehyde solutions where aqueous extraction is used to isolate the aldehyde from a hydroformylation product solution comprising a water-soluble aldehyde, catalyst components and a hydroformylation solvent. Typical catalyst systems are those employed in hydroformylation and may be applied to the preparation of multifunctional amines such as 4-amino-1-butanol and neopentanolamine from water-soluble aldehydes such as 4-hydroxybutanal and hydroxypivaldehyde, respectively. The present invention therefore provides an improved process for the preparation of an amine from a water-soluble aldehyde which comprises contacting in a reaction zone a water-soluble aldehyde, water, ammonia and hydrogen in the presence of a supported ruthenium catalyst. The supported ruthenium catalyst has been found to exhibit activity and selectivity comparable to the nickel catalysts but without leaching or dissolution into the reaction medium. The ruthenium catalyst permits the use of aqueous solutions of the water-soluble aldehyde and/or aqueous ammonia (ammonium hydroxide) to make an amine under mild reductive amination conditions with easy isolation of the amine by simple distillation. Additionally, the relatively mild operating conditions useful in the present process provide obvious economic and safety advantages over a higher pressure system.

The amines produced in accordance with the process are known compounds and may be used as intermediates according to published procedures. For example, AMTHF is a valuable and useful intermediate in the synthesis of pesticides. See, for example, Japanese Patent Publications 10-045739 A2, 09-110848 A2, 09-012565 A2, 08-311063 A2, 08-291170 A2, 08-269053 A2, 08-295684 A2, 08-269035 A2, 08-269034 A2, 08-259553 A2, 08-269052 A2, 08-259554 A2, 08-259563 A2, 08-176132 A2 and 07-173157 A2 and European Patent Application EP 649845 A1.

As has been mentioned above, the FTHF used in the present process may be obtained by hydroformylating 2,5-dihydrofuran (2,5-DHF) using a conventional rhodium-phosphine catalyst. 2,5-DHF may be obtained from 1,3-butadiene by the steps of (1) partially oxidizing butadiene to 3,4-epoxy-1-butene and (2) isomerizing the 3,4-epoxy-1-butene to 2,5-DHF. The selective oxidation of butadiene to 3,4-epoxy-1-butene may be accomplished by the processes described in U.S. Pat. Nos. 5,117,012, 5,312,931 and 5,362,890. The isomerization of 3,4-epoxy-1-butene to 2,5-DHF may be carried out according to the processes disclosed in U.S. Pat. Nos. 5,082,956 and 5,315,019.

DETAILED DESCRIPTION OF THE INVENTION

The process for producing amines in accordance with the present invention is carried out by contacting in a reaction zone a water-soluble aldehyde, water, ammonia and hydrogen in the presence of a supported ruthenium catalyst. The amount of water present typically will give a water:aldehyde weight ratio of about 0.1:1 to 10:1, preferably about 0.2:1 to 2:1. The amount of ammonia present in the reaction zone can vary substantially and normally will be an amount which gives an ammonia:aldehyde mole ratio of at least 1:1 preferably about 2:1 to about 20:1, and most preferably 5:1 to 10:1.

The process may be carried out at a temperature of at least 40° C., preferably about 60 to 150° C. and most preferably about 70 to 120° C. The total reaction pressure is at least 7 bar absolute (bara), preferably in the range of about 7 to 50 bara and most preferably in the range of 10 to 30 bara. The process is carried out in the presence of a catalyst comprising ruthenium deposited on a catalyst support material. Examples of suitable support materials include carbon, aluminum oxide, silica gel, titanium dioxide, zirconium dioxide, magnesium aluminates and magnesium silicates. Carbon is the preferred support. These supported catalysts are available from catalyst suppliers and/or can be prepared by published procedures. The amount of ruthenium on the supported catalysts may be in the range of about 0.1 to 10 weight percent, preferably about 5 to 9 weight percent, based on the total weight of the supported catalyst. The catalysts used in the process preferably contain only ruthenium as the catalytically active metal, i.e., the catalysts consist essentially of ruthenium deposited on a catalyst support material.

The water-soluble aldehydes which may be used in the process of the present invention may contain up to about 10 carbon atoms and may be acyclic or cyclic, carbocylic or heterocyclic, provided that they are water-soluble, i.e., have a water solubility of at least 2 g per liter water, preferably at least 20 g per liter water. The water-soluble aldehydes may exist in aqueous solution in the form of hydrates of the aldehyde. For some aldehydes it may be advantageous to employ a water-miscible co-solvent such as an alkanol, e.g., methanol, ethanol and 2-propanol, to facilitate or increase the solubility of an aldehyde reactant in water. Examples of aldehydes which may be used in the process include 3- and 2-formyltetrahydrofuran, 3-hydroxy-2,2-dimethylpropanal, 3-hydroxy-2-methylpropanal, 4-hydroxybutanal, 3-hydroxybutanal, 3-hydroxypropanal, n-butyraldehyde, isobutyraldehyde, propanal, and acetaldehyde. The process is particularly useful for the preparation of AMTHF from FTHF.

The process may be carried out in a batch, semi-continuous or continuation mode of operation using procedures and techniques well-known in the industry. In batch operation, ammonia and hydrogen may be fed to a pressure vessel containing an aqueous solution of a water-soluble aldehyde and the supported ruthenium catalyst either as a slurry or contained in a wire mesh basket. The catalyst typically is used in such batch operation in an amount which gives a catalyst:aldehyde weight ratio of at least 0.01:1, typically in the range of about 0.05:1 to 0.5:1 and preferably in the range of about 0.1:1 to 0.2:1. The catalyst may be used in the form of a powder or as pellets or extrudates. In continuous operation, ammonia, hydrogen and an aqueous solution of a water-soluble aldehyde may be fed to a pressure vessel, or to a series of pressure vessels, containing one or more fixed beds of a supported catalyst, e.g., a ruthenium-on-carbon catalyst. The reactant solution flows over and through the supported catalyst in the presence of ammonia and hydrogen at elevated pressure and temperature to convert the aldehyde to an amine. While not being bound to any particular theory, it is thought that the conversion of the aldehyde to the amine proceeds via an imine intermediate produced by the reaction of the aldehyde and ammonia. It is important that the imine is hydrogenated quickly to the desired amine product before other reactions occur.

EXAMPLES

The process of the present invention is further illustrated by the following examples. Catalysts were evaluated in 300 mL stirred autoclaves. To simplify loading, ammonium hydroxide (29.3% ammonia) was used. Because water was introduced with the ammonium hydroxide, anhydrous FTHF was used in Examples 1, 2 and 3 and Comparative Example C1. A typical procedure was to add the catalyst, ammonium hydroxide and anhydrous FTHF to a 300 mL autoclave. This was then placed under a nitrogen atmosphere. The autoclave was pressurized with hydrogen to 21 bara (300 psi), the temperature was increased to the desired temperature and the pressure maintained by addition of hydrogen. After the expiration of a predetermined period of time, the autoclave was cooled and depressurized. The product was analyzed by gas chromatography (GC).

COMPARATIVE EXAMPLE C1

Anhydrous FTHF (23.4 g, 0.23 mol), ammonium hydroxide (135 g, 29.3% $NH_3$, 2.3 mol), and molybdenum-promoted Raney-type nickel powder (5.0 g wet) were heated to 60° C. and 21 bara (300 psi) hydrogen for 2 hours. The resulting solution was filtered to remove the catalyst. Removal of most of the water and ammonia by distillation of an aliquot left an oil with a suspended solid. Filtration gave a green powder. Analysis of the oil by gas chromatography showed 82% AMTHF, 5.2% 3-hydroxymethyltetrahydrofuran (HMTHF), 1.4% imine from condensation of AMTHF with FTHF and loss of water (IMINE) and 8.2% di-(tetrahydro-3-furanylmethyl)amine (DTFMA).

EXAMPLE 1

Anhydrous FTHF (25.8 g, 0.26 mol) and ammonium hydroxide (135 g, 29.3% $NH_3$, 2.3 mol) were heated to 100° C. and 21 bara (300 psi) hydrogen pressure for 5.5 hours in the presence of a 7% ruthenium on carbon catalyst (5.0 g) suspended in a basket. Analysis of the resulting solution by gas chromatography showed 90% AMTHF, 4.7% 3-hydroxymethyltetrahydrofuran (HMTHF) and 1.0% di-(tetrahydro-3-furanmethyl)amine (DTFMA).

EXAMPLE 2

Anhydrous FTHF (25.8 g, 0.26 mol), ammonium hydroxide (135 g, 29.3% $NH_3$, 2.3 mol) and 2% ruthenium on carbon catalyst (2 mm extrudates, 5.0 g) were heated to 60°

C. and 21 bara (300 psi) hydrogen for 4 hours. Because only 0.14 mol hydrogen was consumed, the temperature was increased to 100° C. for an additional 4 hours. Analysis of the resulting solution by gas chromatography showed 64.6% AMTHF, 2.6% 3-hydroxymethyltetrahydrofuran (HMTHF) and 17.7% DTFMA.

EXAMPLE 3

Anhydrous FTHF (25.8 g, 0.26 mol), ammonium hydroxide (135 g, 29.3% $NH_3$, 2.3 mol) and 5% ruthenium on alumina powder (Degussa type H2213R/D from Aldrich Chemical Co., 5.0 g) were heated to 100° C. and 21 bara (300 psi) hydrogen for 6.6 hours. Analysis of the resulting solution by gas chromatography showed 87.3% AMTHF, 6.1% 3-hydroxymethyltetrahydrofuran (HMTHF) and 1.1% DTFMA.

EXAMPLE 4

Cyclopropylcarboxaldehyde (CPCA) (92.2% pure, 16.5 g, 0.22 mol) and ammonium hydroxide (135 g, 29.3% $NH_3$, 2.3 mol) with a 7% ruthenium on carbon catalyst (5.0 g) suspended in a basket were heated to 80° C. and 21 bara (300 psi) hydrogen for 5.2 hours. Analysis of the resulting solution by gas chromatography showed 80.6% cyclopropylmethylamine and 7.6% cyclopropylmethanol.

The following examples demonstrate continuous operation of the process wherein an aqueous solution of FTHF (55-59 weight percent concentration), anhydrous ammonia, and hydrogen were fed to a 21 element in-line mixer at the base of a tube-in-shell reactor loaded with catalyst and inerts. The reactor comprised stainless steel tubing having an interior diameter of 21.2 mm (0.834 inch) positioned within a pipe having an interior diameter of 38 mm (1.5 inch) and equipped with inlet and outlet ports for a heating liquid. The catalyst and inerts were placed in the reactor tube between two screens 53.3 cm (21 inches) apart. Thermocouples in a thermowell in the center of the tubing measured temperatures at the inlet and near the middle of the upper and lower reactor zones. Pressure was maintained at 21 bara. After exiting the reactor, the crude product mixture was depressurized and passed through a condenser into a liquid-vapor separator. The vapor was passed through a water scrubber, another condenser, and then through a rotameter. The liquid product was collected and analyzed by gas chromatography. In some cases the product was isolated by distillation with a 15 or 30 tray Oldershaw distillation column with reflux splitter.

COMPARATIVE EXAMPLES C2–C6

Comparative Examples C2–C6 were carried out by feeding an aqueous solution of FTHF, ammonia and hydrogen to the above-described liquid overflow, continuous operation apparatus which contained 170.5 g (about 200 mL) of a supported, molybdenum-promoted, nickel catalyst containing approximately 50 weight percent nickel. The total amount of FTHF aqueous solution fed varied from 246 to 288 g. The operating parameters employed in Comparative Examples C2–C6 are shown in Table I wherein "Temp" is the temperature in ° C. measured in the upper third of the reactor, "FTHF Feed Rate" is the g per hour FTHF reactant fed the reactor, "NH3:FTHF" is the molar ratio of ammonia:FTHF reactant fed to the reactor and "H2:FTHF" is the molar ratio of hydrogen:FTHF reactant fed to the reactor.

TABLE I

| Example | Temp | FTHF Feed Rate | NH3:FTHF | H2:FTHF |
|---|---|---|---|---|
| C2 | 79 | 43.7 | 7.3 | 6.1 |
| C3 | 88 | 42.9 | 7.7 | 6.2 |
| C4 | 88 | 38.3 | 8.7 | 6.5 |
| C5 | 88 | 42.2 | 8.1 | 6.4 |
| C6 | 88 | 37.8 | 8.3 | 7.1 |

The crude liquid product obtained in each of Examples C2–C6 was analyzed by GC and the relative wt % selectivities for AMTHF, HMTHF, Imine and DTFMA were determined. The concentrations of Ni and Mo in the crude product were determined by ion coupled plasma spectroscopy. The crude product contained ammonia which caused problems with the GC analyses. Relative selectivity is the normalization of the 4 major products and disregards 2-(aminomethyl)tetrahydrofuran (tetrahydrofurfurylamine) which forms as a result of 2-formyltetrahydrofuran present in the feed material. These relative selectivities (wt. percentages) and concentrations of Ni and Mo (ppm) are shown in Table II.

TABLE II

| Example | AMTHF | HMTHF | Imine | DTFMA | Ni | Mo |
|---|---|---|---|---|---|---|
| C2 | 87.7 | 1.4 | 9.7 | 1.2 | — | — |
| C3 | 94.8 | 1.4 | 2.5 | 1.2 | 400 | 2.6 |
| C4 | 96.0 | 1.0 | 2.2 | 0.7 | 720 | 6.6 |
| C5 | 83.2 | 0.6 | 15.9 | 0.2 | 640 | 9.1 |
| C6 | 83.7 | 0.7 | 15.4 | 0.2 | 320 | 3.2 |

The liquid products from Examples C2–C4 (1718 g) were combined. Most of the water and ammonia was removed by distillation at atmospheric pressure with a 15 tray Oldershaw column. The remaining material (916 g) was filtered to remove 4.5 g of light green solid. The crude product then was flash distilled to a base temperature of 160° C. at 6 mm Hg vacuum to separate the product from any remaining nickel salts which might catalyze decomposition of the product during distillation. The flashed material (778 g) was distilled under vacuum with a 15 tray Oldershaw column using a reflux ratio of 4:1. AMTHF (654 g, 98.5% pure, 6.38 mol) was obtained for an overall yield of 74% based upon the amount of FTHF fed to the continuous liquid overflow reactor.

EXAMPLES 5–11

The general procedure described above for Comparative Examples C2–C6 was repeated except that the reactor was charged with 65 g (150 mL) of 7% ruthenium-on-carbon catalyst. The operating parameters employed, and the relative selectivities of products obtained, in each of Examples 5–11 are shown in Tables III and IV.

TABLE III

| Example | Temp | FTHF Feed Rate | NH3:FTHF | H2:FTHF |
|---|---|---|---|---|
| 5 | 79 | 30.8 | 10.5 | 8.7 |
| 6 | 79 | 29.7 | 5.4 | 9.1 |
| 7 | 84 | 27.5 | 4.6 | 9.7 |
| 8 | 84 | 26.2 | 4.2 | 2.4 |
| 9 | 84 | 25.8 | 4.0 | 10.4 |
| 10 | 84 | 24.9 | 10.2 | 5.3 |
| 11 | 90 | 28.3 | 9.1 | 4.7 |

TABLE IV

| Example | AMTHF | HMTHF | Imine | DTFMA |
|---|---|---|---|---|
| 5 | 96.0 | 1.6 | 0.4 | 1.9 |
| 6 | 93.4 | 1.8 | 1.4 | 3.5 |
| 7 | 94.7 | 1.6 | 0.4 | 3.3 |
| 8 | 89.0 | 1.3 | 8.1 | 1.6 |
| 9 | 93.9 | 1.8 | 0.5 | 3.8 |
| 10 | 97.1 | 0.9 | 1.2 | 0.9 |
| 11 | 97.6 | 0.9 | 0.6 | 1.0 |

Crude liquid product from Example 5 (1341 g) was distilled using a 15 tray Oldershaw column first at atmospheric pressure to remove most of the water and ammonia and then under vacuum with a reflux ratio of 4:1. AMTHF (552 g, 98.3% pure, 5.37 mol) was obtained for an overall yield of 82.5% based upon the amount of FTHF fed to the continuous liquid overflow reactor. Similarly, material from Examples 6, 7, 9 and 10 were combined and distilled using a 30 plate Oldershaw column to give AMTHF in 89.2% yield with a purity of 98.6%. No solids were observed in either distillation.

The invention has been described in detail with particular reference to preferred embodiments thereof, but it will be understood that variations and modifications can be effected within the spirit and scope of the invention.

I claim:

1. Process for the preparation of an amine from a water-soluble aldehyde which comprises contacting in a reaction zone a water-soluble aldehyde, water, ammonia and hydrogen in the presence of a supported ruthenium catalyst at a temperature of about 60 to 150° C. and a total pressure of about 7 to 50 bar absolute.

2. Process according to claim 1 wherein the reaction zone is maintained at a temperature of about 70 to 120° C. and a total pressure of about 10 to 30 bar absolute; the supported ruthenium catalyst comprises about 0.5 to 10 weight percent ruthenium on a carbon support material; and the water-soluble aldehyde has a water solubility of at least 20 g per liter.

3. Process according to claim 2 wherein the water-soluble aldehyde is selected from 3- and 2-formyltetrahydrofuran, 3-hydroxy-2,2-dimethylpropanal, 3-hydroxy-2-methylpropanal, 4-hydroxybutanal, 3-hydroxybutanal, 3-hydroxypropanal, n-butyraldehyde, isobutyraldehyde, propanal, and acetaldehyde.

4. Process according to claim 2 wherein the amine is 3-(aminomethyl)tetrahydrofuran; the water-soluble aldehyde is 3-formyltetrahydrofuran; and the supported ruthenium catalyst comprises about 5 to 9 weight percent ruthenium on a carbon support material.

5. Process for the preparation of 3-(aminomethyl) tetrahydrofuran which comprises contacting in a reaction zone an aqueous solution of 3-formyltetrahydrofuran, ammonia and hydrogen in the presence of a supported ruthenium catalyst at a temperature of about 60 to 150° C. and a total pressure of about 7 to 50 bar absolute.

6. Process according to claim 5 wherein the reaction zone is maintained at a temperature of about 70 to 120° C. and a total pressure of about 10 to 30 bar absolute; the supported ruthenium catalyst comprises about 0.5 to 10 weight percent ruthenium on a carbon support material; and the amount of water present gives a water:aldehyde weight ratio of about 0.1:1 to 10:1.

7. Process according to claim 5 wherein the reaction zone is maintained at a temperature of about 70 to 120° C. and a total pressure of about 10 to 30 bar absolute; the supported ruthenium catalyst comprises about 5 to 9 weight percent ruthenium on a carbon support material; and the amount of water present gives a water:aldehyde weight ratio of about 0.2:1 to 2:1.

* * * * *